(12) United States Patent
Chao

(10) Patent No.: US 8,135,173 B2
(45) Date of Patent: Mar. 13, 2012

(54) EYE-TRACKING METHOD AND EYE-TRACKING SYSTEM FOR IMPLEMENTING THE SAME

(75) Inventor: Shin-Min Chao, Jhonghe (TW)

(73) Assignee: Utechzone Co., Ltd., Taipei County (TW)

( * ) Notice: Subject to any disclaimer, the term of this patent is extended or adjusted under 35 U.S.C. 154(b) by 434 days.

(21) Appl. No.: 12/550,245

(22) Filed: Aug. 28, 2009

(65) Prior Publication Data

US 2010/0245767 A1    Sep. 30, 2010

(30) Foreign Application Priority Data

Mar. 27, 2009  (TW) ............................... 98110204 A

(51) Int. Cl.
*G06K 9/00*  (2006.01)
(52) U.S. Cl. ......................... 382/103; 351/209; 351/210
(58) Field of Classification Search .................. 382/103; 351/205, 206, 209, 210
See application file for complete search history.

(56) References Cited

U.S. PATENT DOCUMENTS

| | | | | |
|---|---|---|---|---|
| 5,410,376 A * | 4/1995 | Cornsweet et al. | ........... | 351/210 |
| 5,632,742 A * | 5/1997 | Frey et al. | ........... | 606/12 |
| 6,095,648 A * | 8/2000 | Birngruber et al. | ........... | 351/214 |
| 6,299,307 B1 * | 10/2001 | Oltean et al. | ........... | 351/210 |
| 7,001,377 B1 * | 2/2006 | Li | ........... | 606/5 |
| 7,197,165 B2 | 3/2007 | Ryan | ........... | 382/103 |
| 7,391,887 B2 * | 6/2008 | Durnell | ........... | 382/117 |
| 7,832,866 B2 * | 11/2010 | Chao | ........... | 351/209 |

* cited by examiner

*Primary Examiner* — Tom Y Lu
(74) *Attorney, Agent, or Firm* — Stites & Harbison, PLLC; Juan Carlos A. Marquez, Esq

(57) ABSTRACT

An eye-tracking method includes: acquiring an image of an eye of a user captured by an image-capturing module while the user is gazing at a gazing location on a screen module and a pair of light sources emit light toward the eye of the user; determining an angle and an area based on positions of a pupil and two reflected light spots on the eye of the user, wherein the angle and the area correspond to the gazing location; determining coordinates on the screen module based on the angle and the area, wherein the coordinates correspond to the gazing location; and performing an operation associated with the coordinates. An eye-tracking system for implementing the eye-tracking method is also disclosed. A correcting method and a correcting module for the eye-tracking system are further disclosed.

38 Claims, 6 Drawing Sheets

|     |     |     |     |     |     |
|-----|-----|-----|-----|-----|-----|
| PL1 | PL2 | PL3 | PL4 | PL5 | PL6 |
| PL7 | PL8 | PL9 | PL10 | PL11 | PL12 |
| PL13 | PL14 | PL15 | PL16 | PL17 | PL18 |

EYE-TRACKING METHOD AND EYE-TRACKING SYSTEM FOR IMPLEMENTING THE SAME

CROSS-REFERENCE TO RELATED APPLICATION

This application claims priority of Taiwanese Application No. 098110204, filed on Mar. 27, 2009.

BACKGROUND OF THE INVENTION

1. Field of the Invention

This invention relates to an eye-tracking method and system, more particularly to an eye-tracking method and system that is non-invasive.

2. Description of the Related Art

Eye-tracking technology is typically applied to achieve a hands-free interaction between a user and a computer. In particular, this technology detects movement of the eye of the user, identifies a position of the eye of the user based on the movement of the eye detected thereby, and determines a gazing point corresponding to a gazing location on a screen module which the user is gazing at.

Current eye-tracking technologies are divided into two categories, namely invasive and non-invasive eye-tracking technologies.

In a conventional invasive eye-tracking technology, a contact lens mounted with an inductance coil is worn by the user. The contact lens, however, when worn by the user, irritates the eye of the user.

In another conventional invasive eye-tracking technology, electrodes are attached to a periphery of the eye of the user. The electrodes, however, when attached to the periphery of the eye of the user, causes discomfort to the user.

In a conventional non-invasive eye-tracking technology, the user carries a camera and a light source on his/her head. This, however, causes excessive strain on the user's neck, which may eventually lead to neck injury.

In another conventional non-invasive eye-tracking technology, the camera and the light source are placed on a stationary support, such as a table, in front of the user. However, since the user will inevitably move his/her head toward and away from the camera and the light source while using this technology, the gazing point determined by this technology may be erroneous.

In yet another conventional non-invasive eye-tracking technology, such as that disclosed in U.S. Pat. No. 7,197,165, the eye and the eyebrow of the user are first identified from a pre-captured 3D image of the head of the user, and then the eye and the eyebrow are converted into a 2D image from which a position of the eye of the user is identified. This technology, however, incurs high software and hardware implementation costs.

Furthermore, the accuracy of the gazing point determined by the aforementioned conventional technologies is relatively low. In order to solve this problem, a method for correcting the gazing point has been proposed. In this conventional correcting method, four points, each of which corresponds to a position of the eye of the user while the user is gazing at a respective one of four corners of the screen module, are first established, and the gazing point is then interpolated from the pre-established points. Although this conventional method improves the accuracy of the gazing point, greater accuracy is still required for the gazing point.

SUMMARY OF THE INVENTION

Therefore, an object of the present invention is to provide an eye-tracking method and system that can overcome the aforesaid drawbacks of the prior art.

Another object of the present invention is to provide a correcting method and module for the eye-tracking system.

According to a first aspect of the present invention, an eye-tracking method, which is adapted to be implemented by an eye-tracking system, comprises:

A) while a user is gazing at a gazing location on a screen module and a pair of light sources emit light toward an eye of the user, configuring the eye-tracking system to acquire an image of the eye of the user captured by an image-capturing module, the image including a pupil of and a pair of reflected light spots on the eye of the user;

B) configuring the eye-tracking system to determine an angle and an area based on positions of the pupil and the reflected light spots in the image acquired in step A), wherein the angle and the area determined in step B) correspond to the gazing location;

C) configuring the eye-tracking system to determine coordinates on the screen module based on the angle and the area determined in step B), wherein the coordinates determined in step C) correspond to the gazing location; and D) configuring the eye-tracking system to perform an operation associated with the coordinates determined in step C).

According to a second aspect of the present invention, an eye-tracking system comprises an image-analyzing module, a coordinate-converting module, and a processing module. The image-analyzing module is configured to acquire an image of an eye of a user captured by an image-capturing module while the user is gazing at a gazing location on a screen module and a pair of light sources emit light toward the eye of the user, the image including a pupil of and a pair of reflected light spots on the eye of the user, and to determine an angle and an area based on positions of the pupil and the reflected light spots in the image acquired thereby, wherein the angle and the area determined by the image-analyzing module correspond to the gazing location. The coordinate-converting module is coupled to the image-analyzing module, and is configured to determine coordinates on the screen module based on the angle and the area determined by the image-analyzing module, wherein the coordinates determined by the coordinate-converting module correspond to the gazing location. The processing module is coupled to the coordinate-converting module, and is configured to perform an operation associated with the coordinates determined by the coordinate-converting module.

According to a third aspect of the present invention, a correcting method for an eye-tracking system comprises:

A) configuring the eye-tracking system to partition a screen module into predefined locations, each of which has corresponding coordinates;

B) while a user is gazing at one of the predefined locations and a pair of light sources emit light toward an eye of the user, configuring the eye-tracking system to acquire an image of the eye of the user captured by an image-capturing module, the image including a pupil of and a pair of reflected light spots on the eye of the user;

C) configuring the eye-tracking system to determine an angle and an area based on positions of the pupil and the reflected light spots in the image acquired in step B), wherein the angle and the area determined in step C) correspond to the predefined location which the user is gazing at in step B);

D) configuring the eye-tracking system to repeat steps B) and C) until the angles and the areas corresponding to all of the predefined locations are determined; and E) configuring the eye-tracking system to obtain coefficients based on the angles and the areas corresponding to the predefined locations and the corresponding coordinates of the predefined locations, wherein the eye-tracking system determines coordinates on the screen module corresponding to a gazing location on the screen module which the user is gazing at based on the coefficients obtained in step E) and an angle and an area determined thereby from another image of the eye of the user captured by the image-capturing module while the user is gazing at the gazing location, and performs an operation associated with the coordinates determined thereby.

According to a fourth aspect of the present invention, a correcting module for an eye-tracking system comprises first and second controllers and a coefficient calculator. The first controller is configured to indicate one of predefined locations on a screen module. Each of the predefined locations has corresponding coordinates. The second controller is configured to control an image-capturing module to capture an image of an eye of a user while the user is gazing at the indicated one of the predefined locations and a pair of light sources emit light toward the eye of the user. The image includes a pupil and a pair of reflected light spots on the eye of the user. The eye-tracking system is configured to determine an angle and an area corresponding to each of the predefined locations. The eye-tracking system determines the angle and the area corresponding to one of the predefined locations based on positions of the pupil and the reflected light spots in the image captured by the image-capturing module. The angle and the area determined by the eye-tracking system correspond to the indicated one of the predefined locations. The coefficient calculator is configured to obtain coefficients based on the angles and the areas corresponding to the predefined locations and the corresponding coordinates of the predefined locations. The eye-tracking system is further configured to determine coordinates on the screen module corresponding to a gazing location on the screen module which a user is gazing at based on the coefficients obtained by the coefficient calculator and an angle and an area determined thereby from another image of the eye of the user captured by the image-capturing module while the user is gazing at the gazing location, and to perform an operation associated with the coordinates determined thereby.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
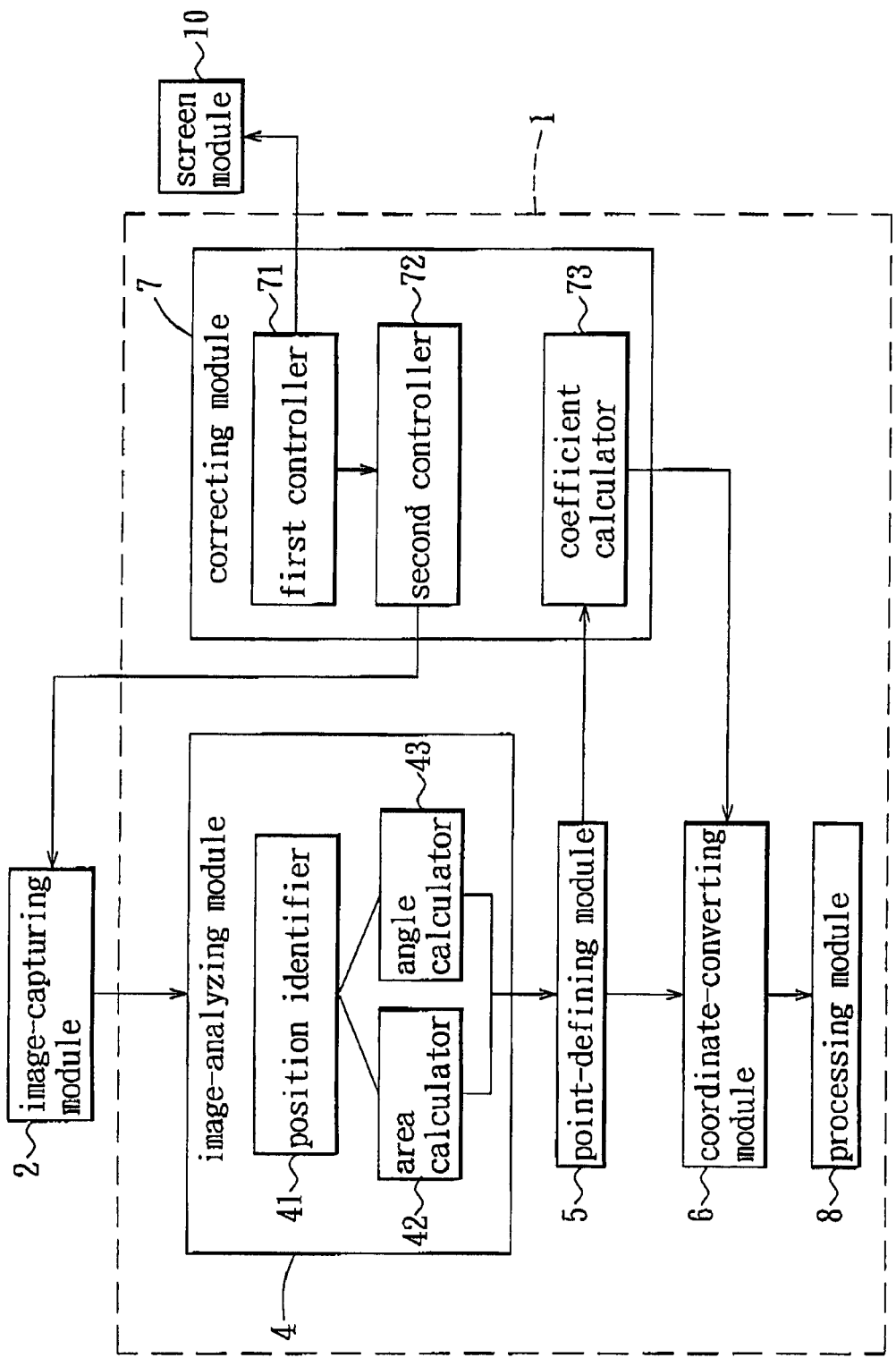
FIG. 1 is a schematic block diagram of the preferred embodiment of an eye-tracking system coupled to an image-capturing module and a screen module according to this invention.

Referring to FIG. 1, the preferred embodiment of an eye-tracking system 1 according to this invention is shown to include an image-analyzing module 4, a point-defining module 5, a coordinate-converting module 6, a processing module 8, and a correcting module 7.

The image-analyzing module 4 is connected to an image-capturing module 2, and includes a position identifier 41, and an area calculator 42 and an angle calculator 43, each of which is connected to the position identifier 41.

The point-defining module 5 is connected to the area calculator 42 and the angle calculator 43 of the image-analyzing module 4.

The coordinate-converting module 6 is connected to the point-defining module 5.

The processing module 8 is connected to the coordinate-converting module 6.

The correcting module 7 includes a first controller 71 connected to a screen module 10, a second controller 72 connected to the first controller 71 and the image-capturing module 2, and a coefficient calculator 73 connected to the point-defining module 5 and the coordinate-converting module 6.

In this embodiment, each of the image-analyzing module 4, the point-defining module 5, the coordinate-converting module 6, and the correcting module 7 is implemented as software.

In an alternative embodiment, each of the image-analyzing module 4, the point-defining module 5, the coordinate-converting module 6, and the correcting module 7 may be implemented as hardware or firmware.

Figure 7A:
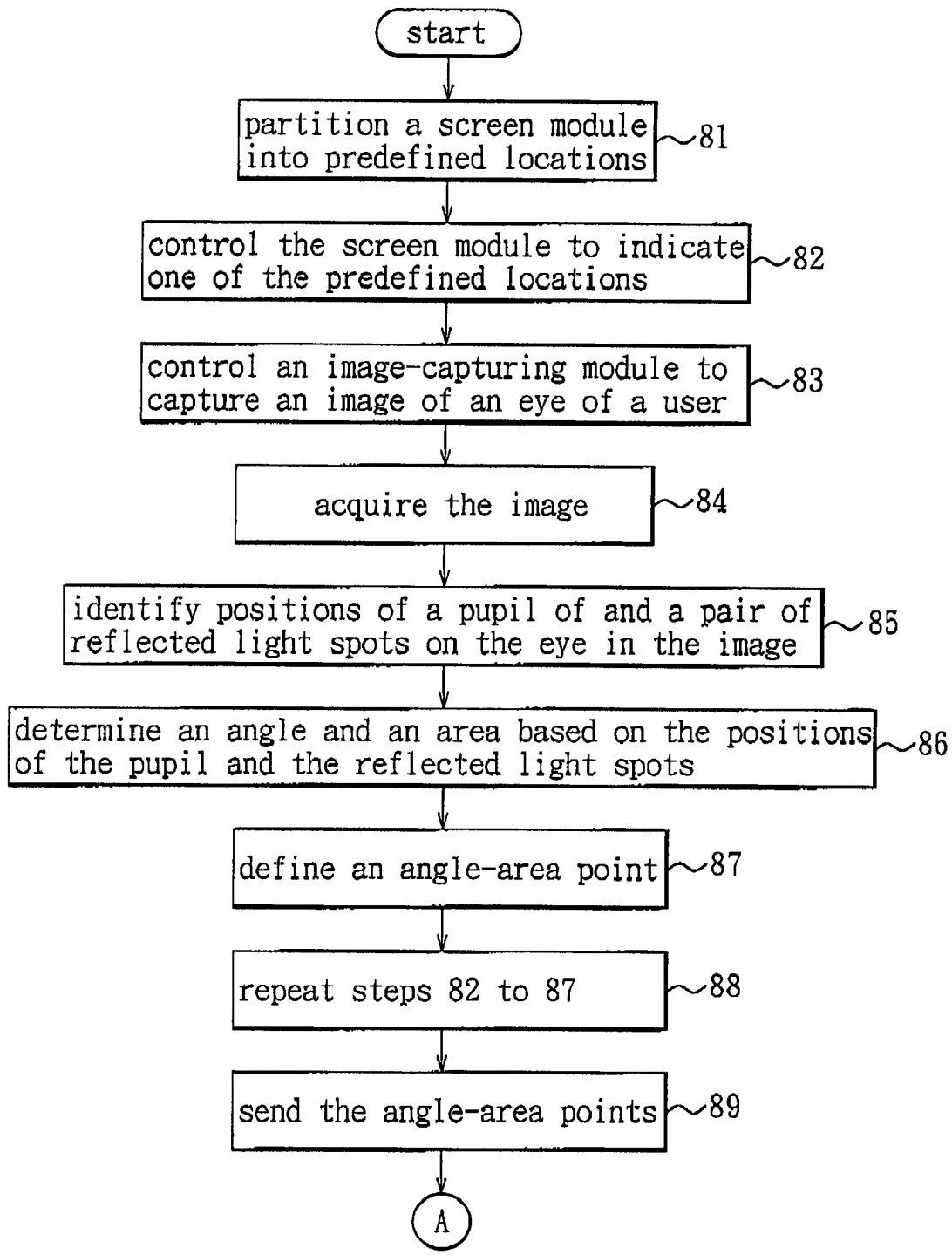
FIGS. 7A and 7B are flow charts of the preferred embodiment of an eye-tracking method to be implemented by the eye-tracking system shown in FIG. 1 according to this invention.
Figure 7B:
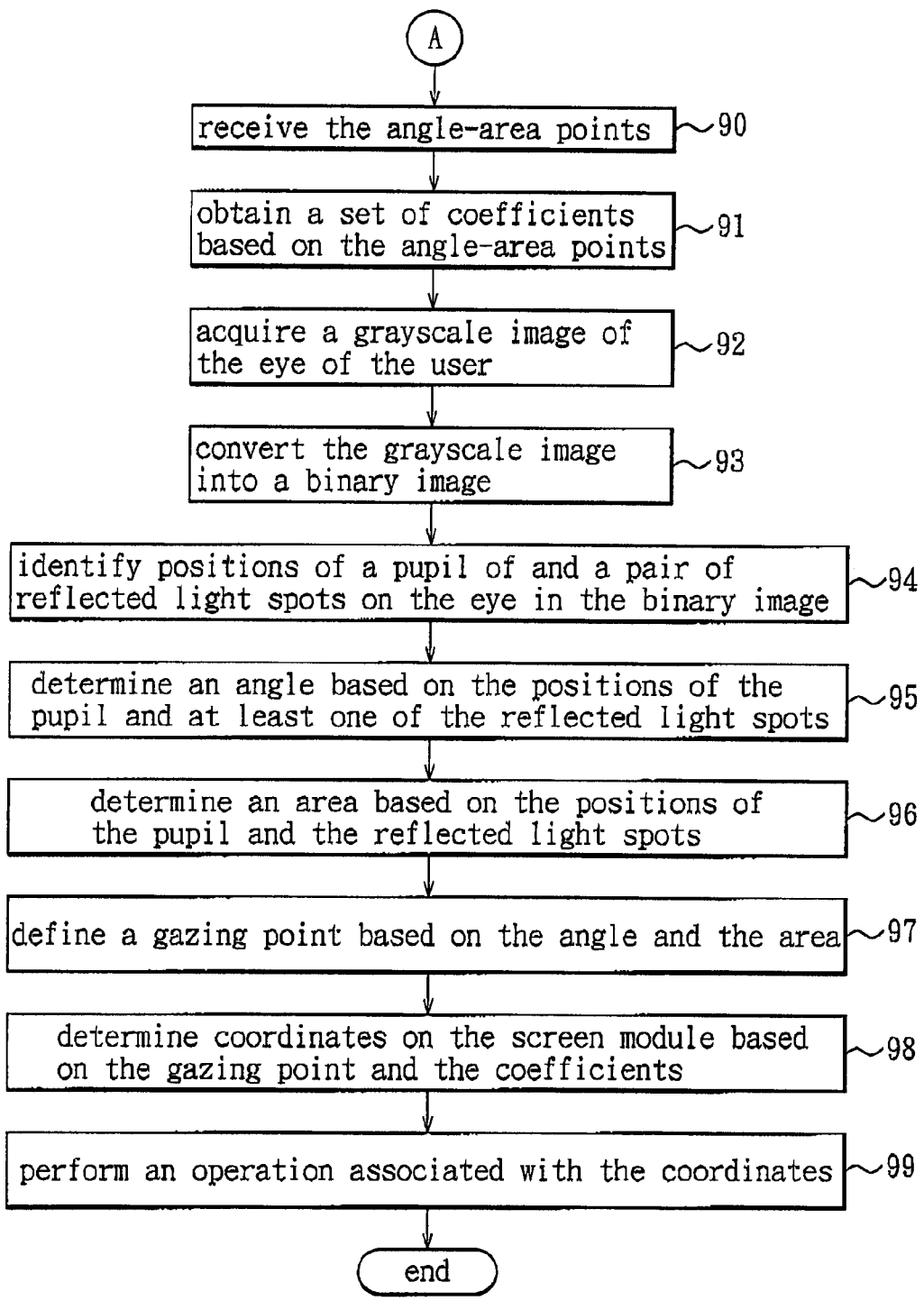

The preferred embodiment of an eye-tracking method to be implemented by the aforementioned eye-tracking system 1 according to this invention will now be described with further reference to FIGS. 7A and 7B.

Figures 3, 4:
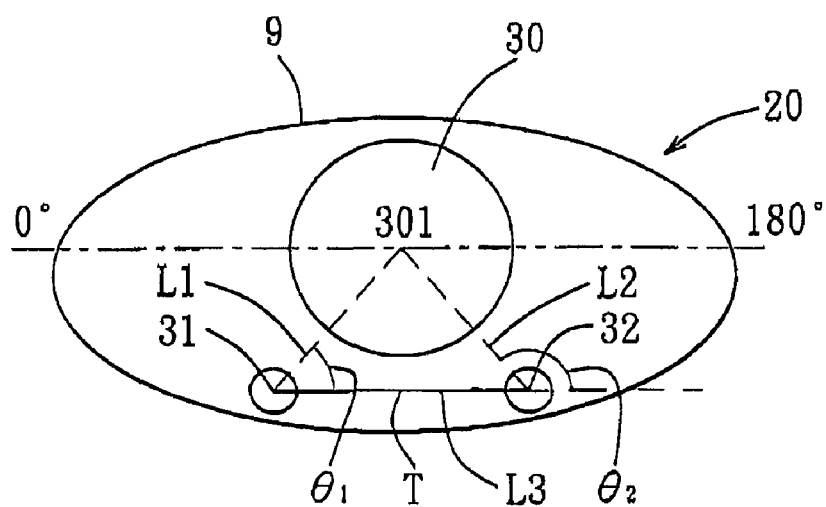
FIG. 3 is a schematic diagram illustrating the screen module when partitioned by the preferred embodiment into eighteen predefined regions.
FIG. 4 is a schematic diagram illustrating the image acquired by the preferred embodiment.

In step 81, as illustrated in FIG. 3, the first controller 71 of the correcting module 7 partitions the screen module 10 into eighteen predefined locations (PL1 to PL18), each of which has corresponding coordinates.

The screen module 10 is partitioned in this step such that four of the predefined locations (PL1, PL6, PL13, PL18) correspond respectively to four corners of the screen module 10 and such that the predefined locations (PL1 to PL18) are arranged in a three by six array.

In step 82, the first controller 71 of the correcting module 7 controls the screen module 10 to indicate one of the predefined locations (PL1 to PL18), e.g., the predefined location (PL1).

Figure 2:
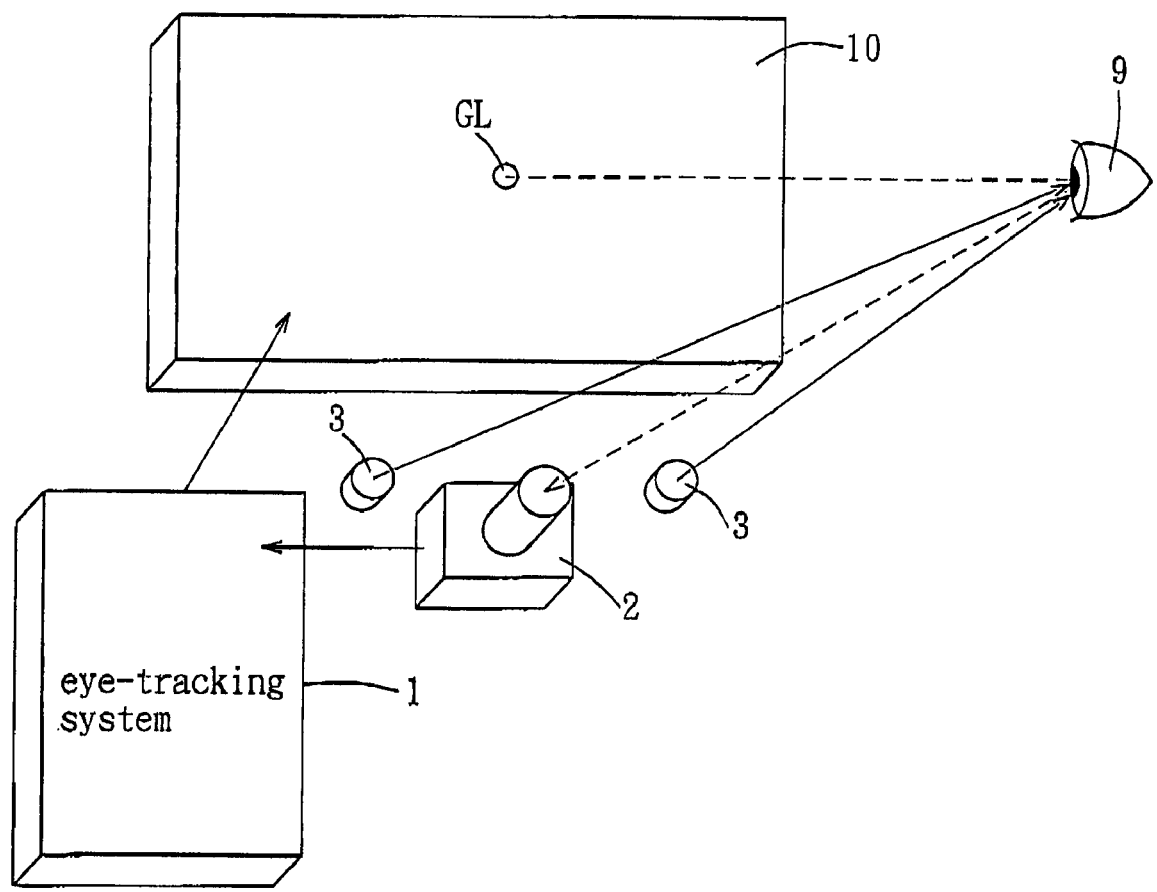
FIG. 2 is a schematic diagram illustrating a state when the preferred embodiment acquires an image of an eye of a user captured by the image-capturing module while the user is gazing at a gazing location on the screen module and a pair of light sources emit light toward the eye of the user.

In step 83, as best shown in FIG. 2, while a user is gazing at the predefined location (PL1) and a pair of light sources 3 emit light toward an eye 9 of the user, the second controller 72 of the correcting module 7 controls, i.e., sends a control signal to, the image-capturing module 2 to capture an image of the eye 9 of the user.

As illustrated in FIG. 4, the image 20 captured by the image-capturing module 2 includes a pupil 30 of and a pair of reflected light spots 31, 32 on the eye 9 of the user.

In step 84, the position identifier 41 of the image-analyzing module 4 acquires the image 20 captured by the image-capturing module 2.

In step 85, the position identifier 41 of the image-analyzing module 4 identifies positions of the pupil 30 and the reflected light spots 31, 32 in the image 20 acquired in step 84.

In step 86, the angle calculator 43 and the area calculator 42 of the image-analyzing module 4 determine an angle and an area, respectively, based on the positions of the pupil 30 and the reflected light spots 31, 32 identified in step 85, wherein the angle and the area determined in this step correspond to the predefined location (PL1).

In step 87, the point-defining module 5 defines an angle-area point, the coordinates of which are the angle and the area determined in step 86, wherein the angle-area point defined in this step corresponds to the predefined location (PL1).

In step 83, the eye-tracking system 1 repeats steps 82 to 87 until the angle-area points corresponding to all of the predefined locations (PL1 to PL18) are defined.

In step 89, the point-defining module 5 of the image-analyzing module 4 sends the angle-area points defined thereby to the coefficient calculator 73 of the correcting module 7.

In step 90, the coefficient calculator 73 of the correcting module 7 receives the angle-area points sent in step 89.

In step 91, the coefficient calculator 73 obtains a set of coefficients based on the angle-area points received in step 90 and the corresponding coordinates of the predefined locations (PL1 to PL18).

The coefficients are obtained in this step using a set of equations, e.g., affine transformation equations, for converting a coordinate system.

In step 92, as best shown in FIG. 2, while the user is gazing at a gazing location (GL) on the screen module 10 and the light sources 3 emit light toward the eye 9 of the user, the position identifier 41 of the image-analyzing module 4 acquires one of continuous grayscale images of the eye 9 of the user captured by the image-capturing module 2.

In step 93, the position identifier 41 of the image-analyzing module 4 converts the grayscale image acquired thereby in step 91 into a binary image.

As illustrated in FIG. 4, the binary image 20 includes a pupil 30 of and a pair of reflected light spots 31, 32 on the eye 9 of the user.

In step 94, the position identifier 41 of the image-analyzing module 4 identifies positions of the pupil 30 and the reflected light spots 31, 32 in the binary image 20.

It is noted that, in step 93, the grayscale image is converted into the binary image 20 using thresholding, in which a pixel in the grayscale image is changed into white when a value of the pixel does not exceed a threshold value or black when the value of the pixel exceeds the threshold value. As such, in this step, the positions of the pupil 30 and the reflected light spots 31, 32 can be easily and quickly identified.

It is also noted that in order to further facilitate the identification of the positions of the pupil 30 and the reflected light spots 31, 32 in this step, an infra-red emitter may be employed to emit infra-red light toward the eye 9 of the user in step 92.

In step 95, the angle calculator 43 of the image-analyzing module 4 determines an angle based on the positions of the pupil 30 and the reflected light spots 31, 32 identified in step 94, wherein the angle determined in this step corresponds to the gazing location (GL).

In this embodiment, with further reference to FIG. 4, step 95 includes the sub-steps of:

i) configuring the angle calculator 43 to define a first line (L1) that passes through a center 301 of the pupil 30 and the reflected light spot 31, a second line (L2) that passes through the center 301 of the pupil 30 and the reflected light spot 32, and a third line (L3) that passes through the reflected light spots 31, 32; and ii) configuring the angle calculator 43 to determine an interior angle ($\theta_1$) between the first and third lines (L1, L3) defined in sub-step i), and an exterior angle ($\theta_2$) between the second and third lines (L2, L3) defined in sub-step i).

The angle ($\theta$) is determined in sub-step i) as an average of the interior and exterior angles ($\theta_1$, $\theta_2$), i.e., $$\theta = (\theta_1 + \theta_2)/2$$

The interior angle ($\theta_1$) is determined in sub-step ii) according to $$\theta_1 = \tan^{-1}[(y0-y1)/(x0-x1)]$$

where x0,y0 are coordinates of the center 301 of the pupil 30, and x1,y1 are coordinates of the reflected light spot 31.

The exterior angle ($\theta_2$) is determined in sub-step ii) according to $$\theta_2 = \tan^{-1}[(y0-y2)/(x0-x2)]$$

where x2,y2 are coordinates of the reflected light spot 32.

In step 96, the area calculator 42 of the image-analyzing module 4 determines an area based on the positions of the pupil 30 and the reflected light spots 31, 32 identified in step 93, wherein the area determined in this step corresponds to the gazing location (GL).

In this embodiment, as illustrated in FIG. 4, step 96 includes the sub-step of configuring the area calculator 42 to define a triangle (T), the vertices of which are the center 301 of the pupil 30 and the reflected light spots 31, 32.

The area (A) determined in step 96 is that of the triangle (T), i.e., $$A = 0.5|(x0(y1)+x1(y2)+x2(y0)-x1(y0)+x2(y1)+x0(y2)|$$

In an alternative embodiment, in which movement of the eye 9 of the user toward and away from the image-capturing module 2 is taken into consideration, as illustrated in FIG. 4, step 96 includes the sub-steps of configuring the area calculator 42 to define a triangle (T), the vertices of which are the center 301 of the pupil 30 and the reflected light spots 31, 32, to determine an area of the triangle (T), and to determine a normalization factor, e.g., one-half of a square of a distance between the reflected light spots 31, 32. In this case, the area is determined in step 96 as the area of the triangle (T) divided by the normalization factor.

Figure 5:
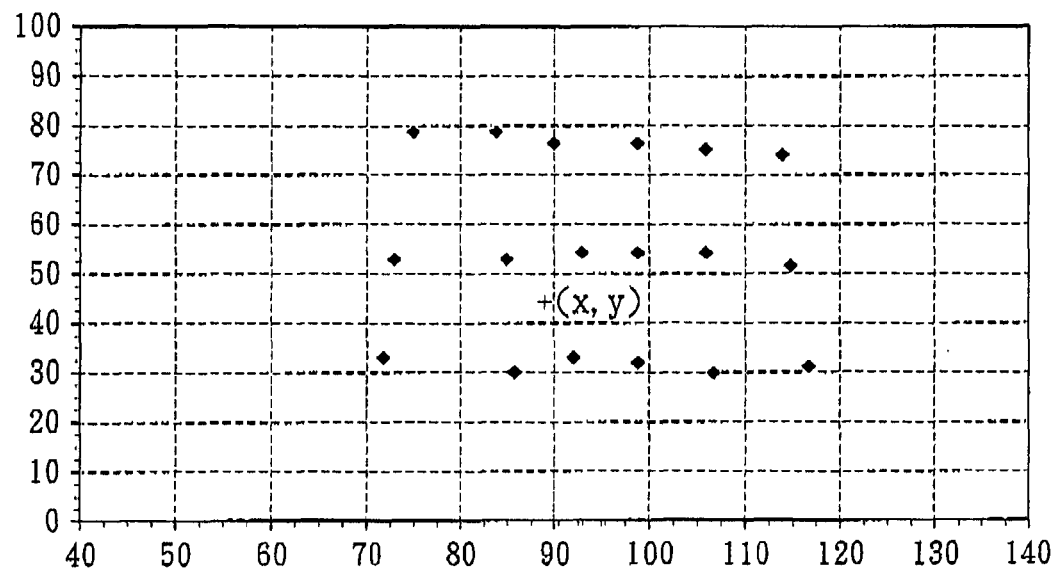
FIG. 5 is a graph representing a gazing point defined by the preferred embodiment.

In step 97, as illustrated in FIG. 5, the point-defining module 5 defines a gazing point (x, y), the coordinates of which are the angle ($\theta$) determined in step 95 and the area (A) determined in step 96, wherein the gazing point (x, y) defined in this step corresponds to the gazing location (GL).

Figure 6:
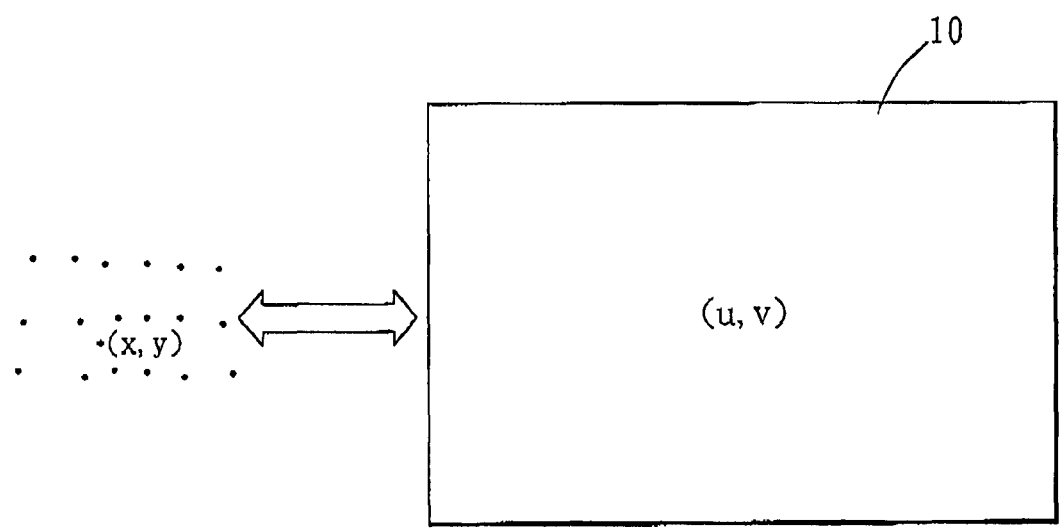
FIG. 6 is a schematic diagram illustrating the gazing point when transformed by the preferred embodiment into coordinates on the screen module.

In step 98 as illustrated in FIG. 6, the coordinate-converting module 6 determines coordinates (u, v) on the screen module 10 based on the gazing point (x, y) defined in step 97 and the coefficients obtained in step 91, wherein the coordinates (u, v) determined in this step correspond to the gazing location (GL).

In this embodiment, the coordinates (u, v) are determined in this step using the affine transformation equations.

In step 99, the processing module 8 performs an operation associated with the coordinates (u, v) determined in step 98. In this step, the processing module 8 moves a cursor (not shown) on the screen module 10 to the coordinates (u, v) determined in step 98.

It is noted that steps 81 to 91 are performed only during the initial use of the eye-tracking system 1 or when it is desired to obtain a new set of coefficients, and steps 92 to 99 are performed during the actual use of the eye-tracking system 1.

Based on experimental results, when a set of the gazing points (x, y) defined in step 97 and a set of the coordinates (u, v) determined in step 98 are plotted on a graph, the gazing points (x, y) form substantially the same shape, e.g., rectangular, as the coordinates (u, v). This indicates that the coordinates (u, v) determined in step 98 by the eye-tracking method of this invention are highly accurate.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. An eye-tracking method adapted to be implemented by an eye-tracking system, said eye-tracking method comprising:
   A) while a user is gazing at a gazing location on a screen module and a pair of light sources emit light toward an eye of the user, configuring the eye-tracking system to acquire an image of the eye of the user captured by an image-capturing module, the image including a pupil of and a pair of reflected light spots on the eye of the user;
   B) configuring the eye-tracking system to determine an angle and an area based on positions of the pupil and the reflected light spots in the image acquired in step A), wherein the angle and the area determined in step B) correspond to the gazing location;
   C) configuring the eye-tracking system to determine coordinates on the screen module based on the angle and the area determined in step B), wherein the coordinates determined in step C) correspond to the gazing location; and
   D) configuring the eye-tracking system to perform an operation associated with the coordinates determined in step C).

2. The eye-tracking method as claimed in claim 1, wherein: step B) includes the sub-steps of
   b1) configuring the eye-tracking system to define a first line that passes through a reference point on the pupil and one of the reflected light spots, a second line that passes through the reference point on the pupil and the other of the reflected light spots, and a third line that passes through the reflected light spots, and
   b2) configuring the eye-tracking system to determine an interior angle between the first and third lines defined in sub-step b1), and an exterior angle between the second and third lines defined in sub-step b1); and
   the angle is determined in step B) as an average of the interior and exterior angles.

3. The eye-tracking method as claimed in claim 1, wherein: step B) includes the sub-step of configuring the eye-tracking system to define a triangle, the vertices of which are a reference point on the pupil and the reflected light spots; and
   the area determined in step B) is that of the triangle.

4. The eye-tracking method as claimed in claim 1, wherein: step B) includes the sub-steps of
   b1) configuring the eye-tracking system to define a triangle, the vertices of which are a reference point on the pupil and the reflected light spots,
   b2) configuring the eye-tracking system to determine an area of the triangle, and
   b3) configuring the eye-tracking system to determine a normalization factor based on a distance between the reflected light spots; and
   the area is determined in step B) as the area determined in sub-step b2) divided by the normalization factor determined in sub-step b3).

5. The eye-tracking method as claimed in claim 4, wherein the normalization factor is based on a square of the distance between the reflected light spots.

6. The eye-tracking method as claimed in claim 5, wherein the normalization factor is determined in sub-step b3) as one-half of the square of the distance between the reflected light spots.

7. The eye-tracking method as claimed in claim 1, wherein the coordinates are determined in step C) using a set of equations for converting a coordinate system.

8. The eye-tracking method as claimed in claim 7, wherein the equations used in step C) are affine transformation equations.

9. The eye-tracking method as claimed in claim 1, further comprising:
   E) configuring the eye-tracking system to obtain a set of coefficients corresponding to predefined locations on the screen module, wherein, in step C), the coordinates are determined based further on the coefficients obtained in step E).

10. The eye-tracking method as claimed in claim 9, wherein step E) includes the sub-steps of:
    e1) configuring the eye-tracking system to partition the screen module into the predefined locations, each of which has corresponding coordinates;
    e2) while the user is gazing at one of the predefined locations and the light sources emit light toward the eye of the user, configuring the eye-tracking system to acquire an image of the eye of the user captured by the image-capturing module, the image including a pupil of and a pair of reflected light spots on the eye of the user;
    e3) configuring the eye-tracking system to determine an angle and an area based on positions of the pupil and the reflected light spots in the image acquired in sub-step e2), wherein the angle and the area determined in sub-step e3) correspond to the predefined location which the user is gazing at in sub-step e2);
    e4) configuring the eye-tracking system to repeat sub-steps e2) and e3) until the angles and the areas corresponding to all of the predefined locations are determined; and
    e5) configuring the eye-tracking system to obtain the coefficients based on the angles and the areas corresponding to the predefined locations and the corresponding coordinates of the predefined locations.

11. The eye-tracking method as claimed in claim 10, wherein, in sub-step e1), four of the predefined locations correspond respectively to four corners of the screen module.

12. The eye-tracking method as claimed in claim 10, wherein, in sub-step e1), the predefined locations are arranged in an array of rows and columns.

13. The eye-tracking method as claimed in claim 10, wherein the coefficients are obtained in sub-step e5) using a set of equations for converting a coordinate system.

14. The eye-tracking method as claimed in claim 1, wherein step D) includes the sub-step of configuring the eye-tracking system to move a cursor on the screen module to the coordinates determined in step C).

15. An eye-tracking system, comprising:
an image-analyzing module configured
to acquire an image of an eye of a user captured by an image-capturing module while the user is gazing at a gazing location on a screen module and a pair of light sources emit light toward the eye of the user, the image including a pupil of and a pair of reflected light spots on the eye of the user, and
to determine an angle and an area based on positions of the pupil and the reflected light spots in the image acquired thereby, wherein the angle and the area determined by said image-analyzing module correspond to the gazing location;
a coordinate-converting module coupled to said image-analyzing module, and configured to determine coordinates on the screen module based on the angle and the area determined by said image-analyzing module, wherein the coordinates determined by said coordinate-converting module correspond to the gazing location; and
a processing module coupled to said coordinate-converting module, and configured to perform an operation associated with the coordinates determined by said coordinate-converting module.

16. The eye-tracking system as claimed in claim 15, wherein;
said image-analyzing module is further configured
to define a first line that passes through a reference point on the pupil and one of the reflected light spots, a second line that passes through the reference point on the pupil and the other of the reflected light spots, and a third line that passes through the reflected light spots, and
to determine an interior angle between the first and third lines, and an exterior angle between the second and third lines; and
the angle is determined by said image-analyzing module as an average of the interior and exterior angles.

17. The eye-tracking system as claimed in claim 15, wherein:
said image-analyzing module is further configured to define a triangle, the vertices of which are a reference point on the pupil and the reflected light spots; and
the area determined by said image-analyzing module is that of the triangle.

18. The eye-tracking system as claimed in claim 15, wherein:
said image-analyzing module is further configured
to define a triangle, the vertices of which are a reference point on the pupil and the reflected light spots,
to determine an area of the triangle, and
to determine a normalization factor based on a distance between the reflected light spots; and
the area is determined by said image-analyzing module as the area of the triangle divided by the normalization factor.

19. The eye-tracking system as claimed in claim 18, wherein the normalization factor determined by said image-analyzing module is based on a square of the distance between the reflected light spots.

20. The eye-tracking system as claimed in claim 18, wherein the normalization factor is determined by said image-analyzing module as one-half of the square of the distance between the reflected light spots.

21. The eye-tracking system as claimed in claim 15, wherein the coordinates are determined by said coordinate-converting module using a set of equations for converting a coordinate system.

22. The eye-tracking system as claimed in claim 21, wherein the equations used by said coordinate-converting module are affine transformation equations.

23. The eye-tracking system as claimed in claim 15, further comprising:
a correcting module coupled to said coordinate-converting module, and configured to obtain a set of coefficients corresponding to predefined locations on the screen module, wherein the coordinates are determined by said coordinate-converting module based further on the coefficients obtained by said correcting module.

24. The eye-tracking system as claimed in claim 23, wherein:
said correcting module is further configured to partition the screen module into the predefined locations, each of which has corresponding coordinates;
said image-analyzing module is further configured to determine an angle and an area corresponding to each of the predefined locations, said image-analyzing module determining the angle and the area corresponding to one of the predefined locations by
acquiring an image of the eye of the user captured by the image-capturing module while the user is gazing at said one of the predefined locations and the light sources emit light toward the eye of the user, the image including a pupil of and a pair of reflected light spots on the eye of the user, and
determining an angle and an area based on positions of the pupil and the reflected light spots in the image acquired thereby, wherein the angle and the area determined by said image-analyzing module correspond to the predefined location which the user is gazing at; and
said correcting module is further configured to obtain the coefficients based on the angles and the areas corresponding to the predefined locations and the corresponding coordinates of the predefined locations.

25. The eye-tracking system as claimed in claim 24, wherein the screen module is partitioned by said correcting module such that four of the predefined locations correspond respectively to four corners of the screen module.

26. The eye-tracking system as claimed in claim 24, wherein the screen module is partitioned by said correcting module such that the predefined locations are arranged in an array of rows and columns.

27. The eye-tracking system as claimed in claim 24, wherein the coefficients are obtained by said correcting module using a set of equations for converting a coordinate system.

28. The eye-tracking system as claimed in claim 15, wherein the operation performed by said processing module includes moving a cursor on the screen module to the coordinates determined by said coordinate-converting module.

29. A correcting method for an eye-tracking system, comprising:
A) configuring the eye-tracking system to partition a screen module into predefined locations, each of which has corresponding coordinates;
B) while a user is gazing at one of the predefined locations and a pair of light sources emit light toward an eye of the user, configuring the eye-tracking system to acquire an image of the eye of the user captured by an image-capturing module, the image including a pupil of and a pair of reflected light spots on the eye of the user;

C) configuring the eye-tracking system to determine an angle and an area based on positions of the pupil and the reflected light spots in the image acquired in step B) wherein the angle and the area determined in step C) correspond to the predefined location which the user is gazing at in step B);

D) configuring the eye-tracking system to repeat steps B) and C) until the angles and the areas corresponding to all of the predefined locations are determined; and E) configuring the eye-tracking system to obtain coefficients based on the angles and the areas corresponding to the predefined locations and the corresponding coordinates of the predefined locations, wherein the eye-tracking system determines coordinates on the screen module corresponding to a gazing location on the screen module which the user is gazing at based on the coefficients obtained in step E) and an angle and an area determined thereby from another image of the eye of the user captured by the image-capturing module while the user is gazing at the gazing location, and performs an operation associated with the coordinates determined thereby.

30. The correcting method as claimed in claim 29, wherein, in step A), four of the predefined locations correspond respectively to four corners of the screen module.

31. The correcting method as claimed in claim 29, wherein, in step E), the coefficients are obtained using a set of equations for converting a coordinate system.

32. The correcting method as claimed in claim 29, wherein, in step A), the predefined locations are arranged in an array of rows and columns.

33. The correcting method as claimed in claim 29, wherein step B) includes the sub-step of configuring the eye-tracking system to control the screen module to indicate one of the predefined locations, wherein the predefined location which the user is gazing at in step B) is the indicated one of the predefined locations.

34. A correcting module for an eye-tracking system, comprising:

a first controller configured to indicate one of predefined locations on a screen module, each of the predefined locations having corresponding coordinates;

a second controller configured to control an image-capturing module to capture an image of an eye of a user while the user is gazing at the indicated one of the predefined locations and a pair of light sources emit light toward the eye of the user, the image including a pupil and a pair of reflected light spots on the eye of the user, wherein the eye-tracking system is configured to determine an angle and an area corresponding to each of the predefined locations, the eye-tracking system determining the angle and the area corresponding to one of the predefined locations based on positions of the pupil and the reflected light spots in the image captured by the image-capturing module, wherein the angle and the area determined by the eye-tracking system correspond to the indicated one of the predefined locations; and a coefficient calculator configured to obtain coefficients based on the angles and the areas corresponding to the predefined locations and the corresponding coordinates of the predefined locations, wherein the eye-tracking system is further configured to determine coordinates on the screen module corresponding to a gazing location on the screen module which a user is gazing at based on the coefficients obtained by said coefficient calculator and an angle and an area determined thereby from another image of the eye of the user captured by the image-capturing module while the user is gazing at the gazing location, and to perform an operation associated with the coordinates determined thereby.

35. The correcting module as claimed in claim 34, wherein said first controller is further configured to partition the screen module into the predefined locations.

36. The correcting module as claimed in claim 35, wherein the screen module is partitioned by said first controller such that four of the predefined locations correspond respectively to four corners of the screen module.

37. The correcting module as claimed in claim 35, wherein the screen module is partitioned by said first controller such that the predefined locations are arranged in an array of rows and columns.

38. The correcting module as claimed in claim 34, wherein the coefficients are obtained by said coefficient calculator using a set of equations for converting a coordinate system.

* * * * *